United States Patent [19]

Maienfisch et al.

[11] Patent Number: 5,439,908
[45] Date of Patent: Aug. 8, 1995

[54] DIAZINYL BUTYRIC ACID AMIDES AND ESTERS

[75] Inventors: Peter Maienfisch, Rodersdorf, Switzerland; Manfred Boger, Weil am Rhein, Germany; Thomas Pitterna, Basel, Switzerland

[73] Assignee: Ciba-Geigy Corporation, Ardsley, N.Y.

[21] Appl. No.: 969,628

[22] Filed: Oct. 30, 1992

[30] Foreign Application Priority Data

Nov. 1, 1991 [CH] Switzerland .......................... 3195/91

[51] Int. Cl.$^6$ .................. A61K 31/50; A61K 31/505; A61K 31/495; C07D 241/18; C07D 239/32; C07D 237/14; C07D 237/18; C07D 237/20
[52] U.S. Cl. ..................... 514/247; 514/252; 514/255; 514/256; 514/269; 514/272; 514/274; 514/275; 544/238; 544/239; 544/240; 544/298; 544/299; 544/300; 544/309; 544/310; 544/311; 544/314; 544/318; 544/319; 544/320; 544/321; 544/322; 544/326; 544/328; 544/329; 544/330; 544/336
[58] Field of Search ............... 514/247, 252, 255, 256, 514/269, 272, 274, 275; 544/238, 239, 240, 298, 299, 300, 310, 311, 314, 318, 319, 320, 321, 322, 326, 328, 329, 330, 336

[56] References Cited

U.S. PATENT DOCUMENTS 4,950,666 8/1990 Peake .................................. 514/227
5,179,121 1/1993 Maienfisch ......................... 514/445

FOREIGN PATENT DOCUMENTS 0002206 8/1979 European Pat. Off. .
0413666 2/1991 European Pat. Off. .
0472497 2/1992 European Pat. Off. .

OTHER PUBLICATIONS

Chem Abstract 002245139, 1979.

*Primary Examiner*—Mukund J. Shah
*Assistant Examiner*—Yogendra N. Gupta
*Attorney, Agent, or Firm*—Marla J. Mathias; Edward McC. Roberts; Kevin T. Mansfield

[57] ABSTRACT

Compounds of the formula

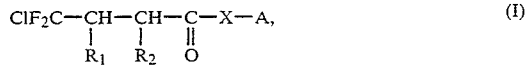

wherein A is a substituted or unsubstituted, aromatic or non-aromatic, monocyclic or bicyclic, heterocyclic radical that is bonded by way of a carbon atom to X; each of $R_1$ and $R_2$, independently of the other, is hydrogen or $C_1$-$C_6$alkyl; X is $NR_3$, O or S; and $R_3$ is hydrogen or $C_1$-$C_4$alkyl, in free form or in salt form, can be used as agrochemical active ingredients and can be prepared in a manner known per se.

13 Claims, No Drawings

DIAZINYL BUTYRIC ACID AMIDES AND ESTERS

The present invention relates to novel derivatives of 4-chloro-4,4-difluoro-butyric acid, to processes for the preparation thereof, to pesticides that comprise those compounds, and to their use in the control of pests.

The 4-chloro-4,4-difluorobutyric acid amides, esters and thioesters according to the invention have the formula

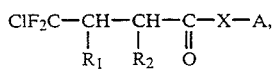  (I)

wherein
A is a substituted or unsubstituted, aromatic or non-aromatic, monocyclic or bicyclic, heterocyclic radical that is bonded by way of a carbon atom to X;
each of $R_1$ and $R_2$, independently of the other, is hydrogen or $C_1$–$C_6$alkyl;
X is $NR_3$, O or S; and
$R_3$ is hydrogen or $C_1$–$C_4$alkyl.

EP-A-0 413 666 and U.S. Pat. No. 4,950,666 propose the use of 4-chloro-4,4-difluoro-butyric acid derivatives as active ingredients in pesticides. The biological properties of the compounds described in those publications are not, however, entirely satisfactory for the area of pest control, hence the need to provide other compounds having pesticidal properties; this problem is solved according to the invention by the provision of the present compounds I.

The compounds I of the invention include acid addition salts, especially agrochemically acceptable acid addition salts. Examples of suitable (inorganic or organic) acids are hydrochloric acid, hydrobromic acid, sulfuric acid, phosphoric acid, nitric acid, acids having the same central atom and a higher or lower oxidation stage, such as perchloric acid, nitrous acid or phosphorous acid, acetic acid and succinic acid.

Preferred embodiments within the context of the invention are
(1) a compound of formula I wherein $R_1$ is hydrogen;
(2) a compound of formula I wherein $R_2$ is hydrogen;
(3) a compound of formula I wherein X is $NR_3$ or S and $R_3$ is hydrogen or $C_1$–$C_4$alkyl, especially a compound of formula I wherein X is NH or S, preferably a compound of formula I wherein X is NH;
(4) a compound of formula I wherein the radical A that is bonded by way of a carbon atom to X is selected from the group of radicals, consisting of

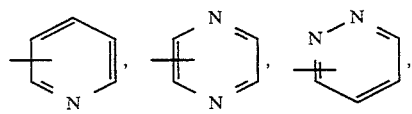

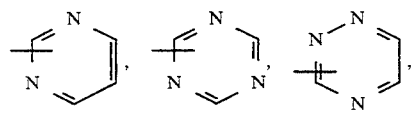

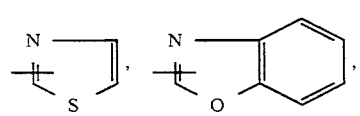

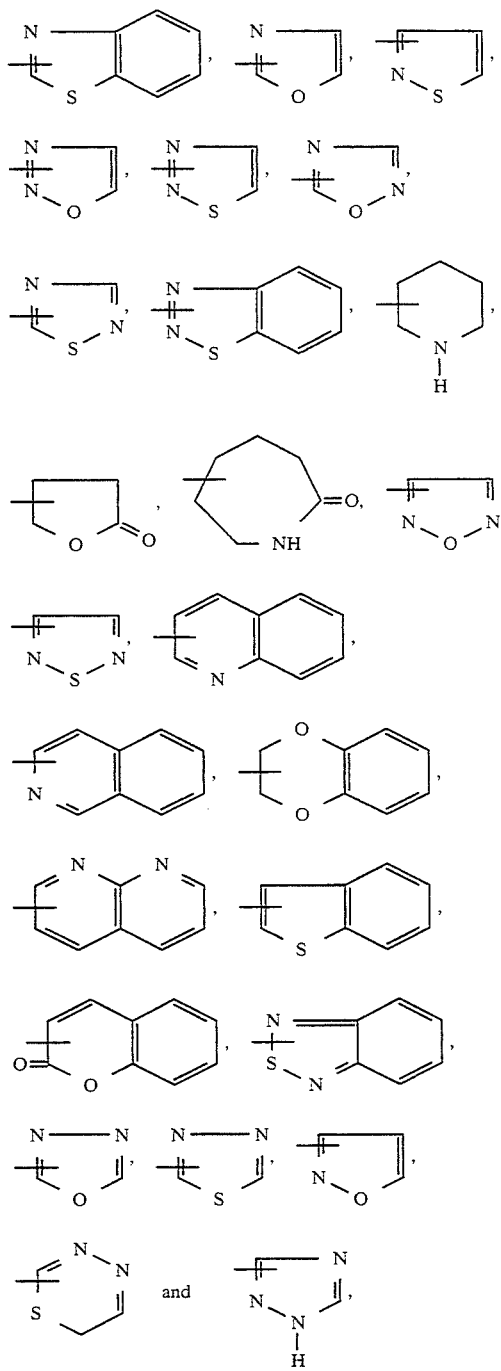

and is unsubstituted or carries one, two, three or four substituents selected from the group, consisting of halogen, $C_1$–$C_6$alkyl, $C_1$–$C_4$haloalkyl having from 1 to 9 halogen atoms, $C_1$–$C_4$alkoxy, $C_1$–$C_4$haloalkoxy having from 1 to 9 halogen atoms, nitro, cyano, $C_1$–$C_4$-alkoxycarbonyl, di($C_1$–$C_4$alkyl)amino, phenyl, benzyl, pyridyl, thienyl and phenyl, benzyl, pyridyl and thienyl each mono-substituted by halogen, $C_1$–$C_4$alkyl, $C_1$–$C_4$-haloalkyl having from 1 to 9 halogen atoms, $C_1$–$C_4$alkoxy, nitro or by cyano, especially a compound of formula I wherein the radical A that is bonded by way of a carbon atom to X is selected from the group of radicals, consisting of

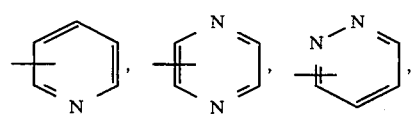

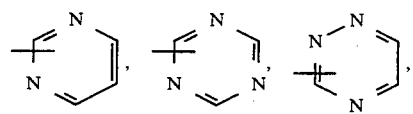

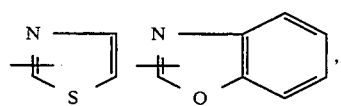

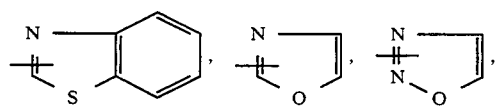

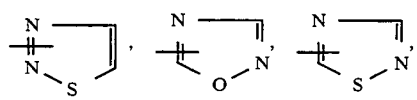

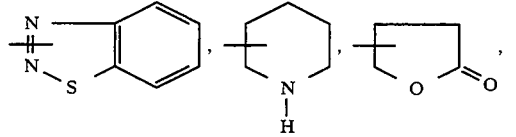

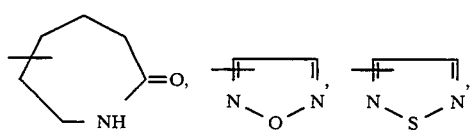

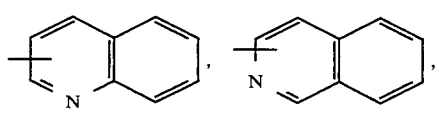

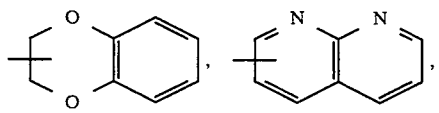

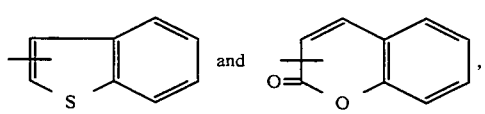

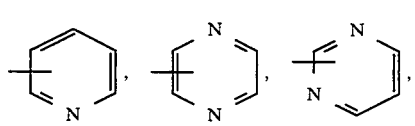

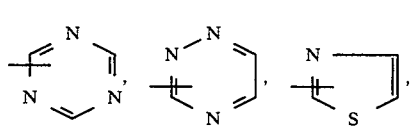

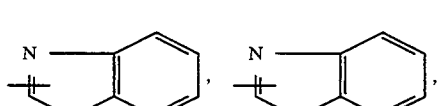

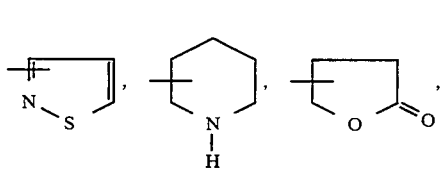

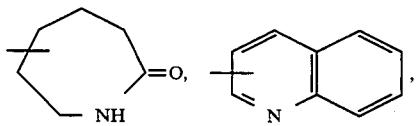

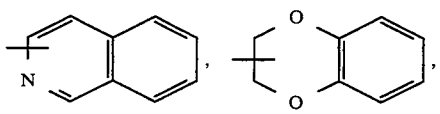

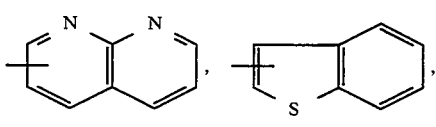

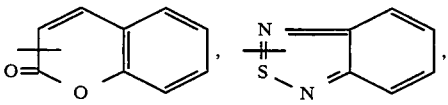

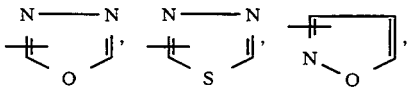

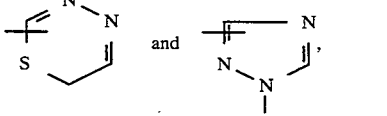

and is unsubstituted or carries one or two substituents selected from the group, consisting of halogen, $C_1$–$C_6$alkyl, $C_1$–$C_4$haloalkyl having from 1 to 9 halogen atoms, $C_1$–$C_4$alkoxy, $C_1$–$C_4$haloalkoxy having from 1 to 9 halogen atoms, nitro, cyano, $C_1$–$C_4$alkoxycarbonyl, di($C_1$–$C_4$alkyl)amino, phenyl, benzyl, pyridyl, thienyl and phenyl, benzyl, pyridyl and thienyl each mono-substituted by halogen, $C_1$–$C_4$alkyl, $C_1$–$C_4$haloalkyl having from 1 to 9 halogen atoms, $C_1$–$C_4$alkoxy, nitro or by cyano, especially a compound of formula I wherein the radical A that is bonded by way of a carbon atom to X is selected from the group of radicals, consisting of and is unsubstituted or carries one, two, three or four substituents selected from the group, consisting of halogen, $C_1$–$C_6$alkyl, $C_1$–$C_4$haloalkyl having from 1 to 9 halogen atoms, $C_1$–$C_4$alkoxy, nitro, $C_1$–$C_4$alkoxycarbonyl, di($C_1$–$C_4$alkyl)amino, phenyl, benzyl, pyridyl and thienyl, especially a compound of formula I wherein the radical A that is bonded by way of a carbon atom to X is selected from the group of radicals, consisting of

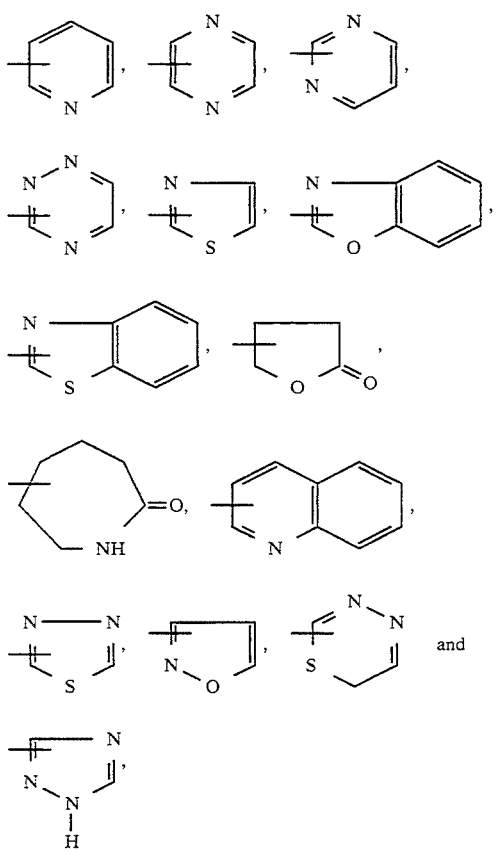

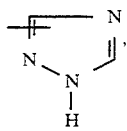

and is unsubstituted or carries one, two or three substituents selected from the group, consisting of halogen, methyl, pyridyl and thienyl, especially a compound of formula I wherein the radical A that is bonded by way of a carbon atom to X is selected from the group of radicals, consisting of

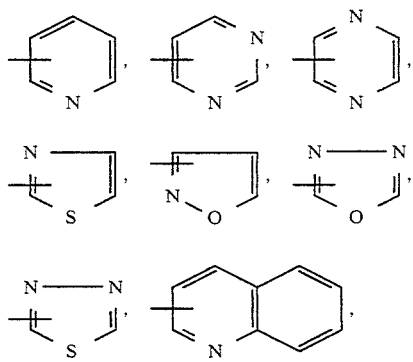

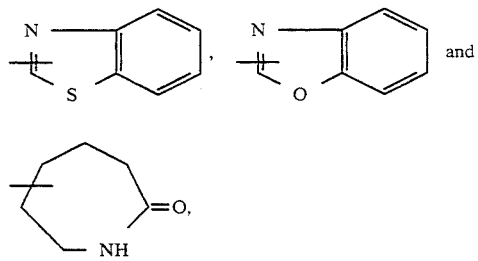

and is unsubstituted or mono-substituted by halogen, methyl, pyridyl or thienyl, especially a compound of formula I wherein the radical A is selected from the group of radicals, consisting of pyrid-2-yl, pyrid-3-yl, pyrimidin-2-yl, pyrazin-2-yl, thiazol-2-yl, isoxazol-3-yl, 1,3,4-oxadiazol-2-yl, 1,3,4-thiadiazol-2-yl, benzoxazol-2-yl, benzothiazol-2-yl and quinolin-3-yl, which radicals are unsubstituted or mono-substituted by halogen, methyl, pyridyl or thienyl, especially a compound of formula I wherein the radical A is unsubstituted pyrid-2-yl or unsubstituted thiazol-2-yl;

(5) a compound of formula I wherein $R_1$ is hydrogen, $R_2$ is hydrogen, X is NH or S and the radical A is selected from the group of radicals, consisting of pyrid-2-yl, pyrid-3-yl, pyrimidin-2-yl, pyrazin-2-yl, thiazol-2-yl, isoxazol-3-yl, 1,3,4-oxadiazol-2-yl, 1,3,4-thiadiazol-2-yl, benzoxazol-2-yl, benzothiazol-2-yl and quinolin-3-yl, which radicals are unsubstituted or mono-substituted by halogen, methyl, pyridyl or thienyl;

(6) a compound of formula I wherein $R_1$ is hydrogen, $R_2$ is hydrogen, X is NH and the radical A is unsubstituted pyrid-2-yl or unsubstituted thiazol-2-yl.

Special preference is given within the context of the invention to the compounds of formula I mentioned in Examples P1 and P2.

Unless otherwise defined, the general terms used hereinbefore and hereinafter have the following definitions.

and is unsubstituted or carries one, two or three substituents selected from the group, consisting of halogen, $C_1$–$C_6$alkyl, nitro, phenyl, pyridyl and thienyl, especially a compound of formula I wherein the radical A that is bonded by way of a carbon atom to X is selected from the group of radicals, consisting of

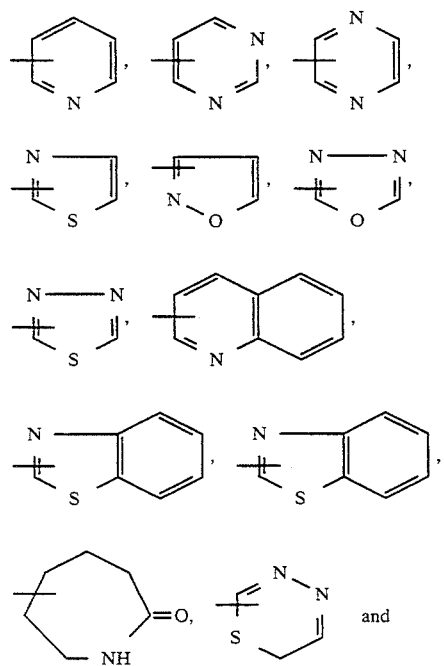

Halogen atoms that are suitable as substituents are fluorine and chlorine and also bromine and iodine, with fluorine, chlorine and bromine being preferred and with fluorine and chlorine being especially preferred. Halogen is to be understood here as being an independent substituent or part of a substituent, as in haloalkyl or haloalkoxy.

Unless otherwise defined, the carbon-containing groups and compounds each contain preferably from 1 up to and including 4, especially 1 or 2, carbon atoms.

Alkyl—as a group per se and as a structural element of other groups and compounds, for example of alkoxy, dialkylamino, haloalkyl, haloalkoxy and alkoxycarbonyl—is either straight-chain or branched, in each case according to the number of carbon atoms present in the corresponding group or compound. Examples of alkyl that may be mentioned are methyl, ethyl, propyl, isopropyl, butyl, isobutyl, sec-butyl and tert-butyl as as well as pentyl, hexyl and their respective isomers.

Halo-substituted groups, i.e. haloalkyl and haloalkoxy, may be partially halogenated or perhalogenated. Examples of haloalkyl—as a group per se or as a structural element of other groups and compounds, such as of haloalkoxy—are methyl substituted by from one to three substituents selected from fluorine, chlorine and bromine, such as $CHF_2$ or $CF_3$; ethyl substituted by from one to five substituents selected from fluorine, chlorine and bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl substituted by from one to seven substituents selected from fluorine, chlorine and bromine, such as $CH_2CHBrCH_2Br$, $CF_2CHFCF_3$, $CH_2CF_2CF_3$ or $CH(CF_3)_2$; and butyl substituted by from one to nine substituents selected from fluorine, chlorine and bromine, or one of its isomers, such as $CF(CF_3)CHFCF_3$ or $CH_2(CF_2)_2CF_3$.

The two alkyl groups present in dialkylamino can be identical or different.

The invention relates also to a process for the preparation of the compounds of formula I, in free form or in salt form, for example wherein a) a compound of the formula

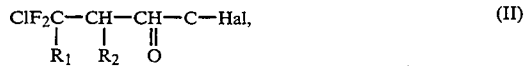

wherein $R_1$ and $R_2$ are as defined for formula I and Hal is halogen, preferably chlorine or bromine, is reacted in the presence of a base with a compound of the formula

HX—A     (III)

wherein A and X are as defined for formula I, or with a salt thereof, or b) a compound of the formula

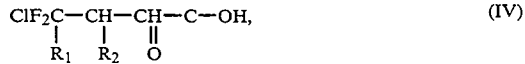

wherein $R_1$ and $R_2$ are as defined for formula I, is reacted in the presence of a condensation agent with a compound of formula III, or with a salt thereof, or c) a compound of the formula

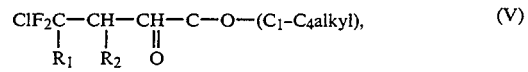

wherein $R_1$ and $R_2$ are as defined for formula I, is reacted with a compound of the formula III, or with a salt thereof, and in each case, if desired, a free compound of formula I obtainable in accordance with the process is converted into a salt or a salt of a compound of formula I obtainable in accordance with the process is converted into the free compound of formula I or into a different salt.

Examples of suitable bases for Process variant a) are organic bases, for example pyridine, 4-dimethylaminopyridine, lutidine, collidine, trialkylaminea, N,N-dialkylaniline or bicyclic non-nucleophilic bases, such as 1,4-diazabicyclo[2.2.2]octane (DABCO), 1,5-diazabicyclo[4.3.0]non-5-ene (DBN) and 1,8-diazabicyclo[5.4.0]undec-7-ene (DBU). The reaction is generally carried out at temperatures of from −30° to +70° C. preferably from −10° to +50° C., advantageously in the presence of an inert solvent or solvent mixture. Examples of suitable solvents are aliphatic and aromatic hydrocarbons, such as benzene, toluene, xylenes, petroleum ether or hexane; halogenated hydrocarbons, such as chlorobenzene, dichloromethane, ethylene chloride, trichloromethane, tetrachloromethane or tetrachloroethylene; ethers and ethereal compounds, such as dialkyl ethers (diethyl ether, diisopropyl ether, tert-butyl methyl ether, etc.), anisole, dioxane or tetrahydrofuran; nitrics, such as acetonitrile or propionitrile; esters, such as ethyl acetate, propyl acetate or butyl acetate; ketones, such as acetone, diethyl ketone or methyl ethyl ketone; and mixtures of such solvents with one another. The reaction can, however, also be carried out in an excess of one of the above-mentioned bases, or a second equivalent or a larger excess of compound III can be used instead of the base.

Examples of suitable condensation agents for Process variant b) are phosphorous acid dichloride phenyl ester, benzene-phosphonic acid dichloride, 2,4,6-trichloro-1,3,5-triazine, 5,6-dioxo-1,3-diphenyl-5,6-dihydro-<thieno[3,4-b]-1,4-dioxine>2,2-dioxide, carbonic acid diimidazolide, dicyclohexylcarbodiimide, aluminium oxide, titanium (IV) chloride, 2,2,4,4,6,6-hexachloro-1,3,5,2,4,6-triazatriphosphorine and chloroformic acid lower alkyl esters, such as chloroformic acid isobutyl ester. The reaction is preferably carried out in the presence of a base, for example in the presence of an organic amine, for example a trialkylamine (such as trimethylamine, triethylamine, tripropylamine or diisopropylethylamine), a pyridine (such as pyridine, 4-dimethylaminopyridine or 4-pyrrolidinopyridine), a morpholine (such as N-methylmorpholine) or an N,N-dialkylaniline (such as N,N-dimethylaniline or N-methyl-N-ethylaniline). The reaction is advantageously carried out in the presence of an inert solvent or solvent mixture and at temperatures of from −30° to +70° C., preferably from −10° to +50° C. Examples of suitable solvents are aliphatic and aromatic hydrocarbons, such as benzene, toluene, xylenes, petroleum ether or hexane; halogenated hydrocarbons, such as chlorobenzene, dichloromethane, ethylene chloride, trichloromethane, tetrachloromethane or tetrachloroethylene; ethers and ethereal compounds, such as dialkyl ethers (diethyl ether, diisopropyl ether, tert-butyl methyl ether, etc.), anisole, dioxane or tetrahydrofuran; nitriles, such as acetonitrile or propionitrile; esters, such as ethyl acetate, propyl acetate or butyl acetate; and mixtures of such solvents with one another.

In Process variant c), the reactants are advantageously reacted in an inert solvent or solvent mixture. Examples of suitable solvents are aliphatic and aromatic hydrocarbons, such as benzene, toluene, xylenes, petroleum ether or hexane; halogenated hydrocarbons, such as chlorobenzene, dichloromethane, ethylene chloride, trichloromethane, tetrachloromethane or tetrachloroethylene; ethers and ethereal compounds, such as dialkyl ethers (diethyl ether, diisopropyl ether, tert-butyl methyl ether, etc.), anisole, dioxane or tetrahydrofuran; nitriles, such as acetonitrile or propionitrile; alcohols, such as methanol, ethanol, propanol or isopropanol; and water. The amine component III is advantageously used in excess. The reaction temperatures are generally from 0° to +120° C.

The conversion of free compounds I into salts and of salts into free compounds I or into different salts is effected in customary manner, for example by treating a free compound I with an acid, or treating a salt with a base.

Compounds II, III IV and V are known or can be prepared by analogy with the known compounds.

The compounds I according to the invention are valuable active ingredients in pest control while being well tolerated by warm-blooded animals, fish and plants. The compounds according to the invention are effective especially against insects and arachnids which occur on useful plants and ornamentals in agriculture and horticulture, especially in rice, cotton, vegetable and fruit crops, and in forestry. The compounds I are especially suitable for controlling insects in rice, fruit and vegetable crops, especially for controlling plant-destructive sucking insects, such as aphids and cicadas, for example Aphis craccivora, Nilaparvata lugens and Nephotettix cincticeps. The compounds according to the invention can also be used in the protection of stored goods and material stocks and in the hygiene sector, especially the protection of domestic animals and productive livestock. The compounds I are effective against all or individual development stages of normally sensitive and also resistant species of pest. Their action may manifest itself, for example, in the death of the pests, which occurs immediately or not until some time later, for example during moulting, or in reduced oviposition and/or a reduced hatching rate.

The above-mentioned pests include:
of the order Lepidoptera, for example
Acleris spp., Adoxophyes spp., Aegeria spp., Agrotis spp., *Alabama argillaceae*, Amylois spp., *Anticarsia gemmatalis*, Archips spp., Argyrotaenia spp., Autographa spp., *Busseola fusca, Cadra cautella, Carposina nipponensis*, Chilo spp., Choristoneura spp., *Clysia ambiguella*, Cnaphalocrocis spp., Cnephasia spp., Cochyllis spp., Coleophora spp., *Crocidolomia binotalis, Cryptophelebia leucotreta*, Cydia spp., Diatraea spp., *Diparopsis castanea*, Earias spp., Ephestia spp., Eucosma spp., *Eupoecilia ambiguella*, Euproctis spp., Euxoa spp., Grapholita spp., *Hedya nubiferana*, Heliothis spp., *Hellula undaliz, Hyphantria cunea, Keiferia lycopersicella, Leucoptera scitella*, Lithocollethis spp., *Lobesia botrana*, Lymantria spp., Lyonetia spp., Malacosoma spp., *Mamestra brassicae, Maraluca sexta*, Operophtera spp., *Ostrinia nubilalis*, Pammene spp., Pandemis spp., *Panolis flammea, Pectinophora gossypiella, Phthorimaea operculella, Pieris rapae*, Pieris spp., *Plutella xylostella*, Prays spp., Scirpophaga spp., Sesamia spp., Sparganothis spp., Spodoptera spp., Synanthedon spp., Thaumetopoea spp., Tortrix spp., *Trichoplusia ni* and Yponomeuta spp.;
of the order Coleoptera, for example
Agriotes spp., Anthonomus spp., *Atemaria linearis. Chaetoenema tibialis*, Cosmopolites spp., Curculio spp., Dermestes spp., Diabrotica spp., Epilachna spp., Eremnus spp., *Leptinotarsa decemilineata*, Lissorhoptrus spp., Melantha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribelium spp. and Trogorma spp.;
of the order Orthoptera, for example
Blatta spp., Blattella spp., Gryllotalpa spp., *Leucophaea maderae*, Locusta spp., Periplaneta spp. and Schistocerca spp.;
of the order Isoptera, for example
Reticulitermes spp.;
of the order Psocoptera, for example
Liposcelis spp.;
of the order Anoplura, for example
Haematopinus spp., Linognathus spp., Pediculus spp., Pemphigus spp. and Phylloxera spp.;
of the order Mallophaga, for example
Damalinea spp. and Trichodectes spp.;
of the order Thysanoptera, for example
Frankliniella spp., Hercinothrips spp., Taeniothrips spp., *Thrips palmi, Thrips tabaci* and *Scirtothrips aurantii*;
of the order Heteroptera, for example
Cimex spp., *Distantiella theobroma*, Dysdercus spp., Euchistus spp., Eurygaster spp., Leptocorisa spp., Nezara spp., Piesma spp., Rhodnius spp., *Sahlbergella singularis*, Scotinophara spp. and Triatoma spp.;
of the order Homoptera, for example
*Aleurothrixus floccosus, Aleyrodes brassicae*, Aonidiella spp., Aphididae, Aphis spp., Aspidiotus spp., *Bemisia tabaci*, Ceroplaster spp., *Chrysomphalus aonidium, Chrysomphalus dictyospermi, Coccus hesperidum*, Empossca spp., *Eriosoma larigerum*, Erythroneura spp., Gascardia spp., Laodelphax spp., *Lecanium corni*, Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., Pulvinaria aethipica, Quadrospidiotus spp., Rhopalosiphum spp., Saissetia spp., Scaphoideus spp., Schizaphis spp., Sitobion spp., *Trialeurodes vaporariorum, Trioza erytreae* and *Unaspis citri*;
of the order Hymenoptera, for example
Acromyrmex, Atta spp., Cephus spp., Diprion spp., Diprionidae, *Gilpinia polytoma*, Hoplocampa spp., Lasius spp., *Monomorium pharaonis*, Neodiprion spp., Solenopsis spp. and Vespa spp.;
of the order Diptera, for example
Aedes spp., *Antherigona soccata, Bibio hortulanus, Calliphora erythrocephala*, Ceratitis spp., Chrysomyia spp., Culex spp., Cuterebra spp., Dacus spp., *Drosophila melanogaster*, Fannia spp., Gastrophilus spp., Glossina spp., Hyporma spp., Hyppoboaca spp., Liriomyza spp., Lucilia spp., Melanagromyza spp., Musca spp., Oestrus spp., Orseolia spp., *Oscinella frit, Pegomyia hyoscyami*, Phorbia spp., *Rhagoletis pomonella*, Sciara spp., Stomoxys spp., Tabanus spp., Tannia spp. and Tipula spp.;
of the order Siphonaptera, for example
Ceratophyllus spp. and *Xenopsylla cheopis*;
of the order Thysanura, for example
*Lepisma saccharina* and
of the order Acarina, for example

*Acarus siro, Aceria sheldoni, Aculus schlechtendali,* Amblyomma spp., Argas spp., Boophilus spp., Brevipalpus spp., *Bryobia practiosa,* Calipitrimerus spp., Chorioptes spp., *Dermanyssus gallinae, Eotetranychus carpini,* Eriophyes spp., Hyalomma spp., Ixodes spp., *Olygonychus pratensis,* Ornithodoros spp., Panonychus spp., *Phyllocoptruta oleivora, Polyphagotarsonemus latus,* Psoroptes spp., Rhipicephalus spp., Rhizoglyphus spp., Sarcoptes spp., Tarsonemus spp. and Tetranychus spp..

The good pesticidal activity of the compounds I according to the invention corresponds to a mortality of at least 50–60% of the mentioned pests.

The activity of the compounds I of the invention and of the compositions comprising them can be substantially broadened and adapted to prevailing circumstances by the addition of other insecticides and/or acaricides. Examples of suitable additives include representatives of the following classes of compounds: organophosphorus compounds, nitrophenols and derivatives thereof, formamidines, ureas, carbamates, pyrethroids, chlorinated hydrocarbons, and Bacillus thuringiensis preparations.

The compounds I are used in unmodified form or, preferably, together with the adjuvants conventionally employed in formulation technology, and can therefore be formulated in known manner e.g. into emulsifiable concentrates, directly sprayable or dilutable solutions, dilute emulsions, wettable powders, soluble powders, dusts, granules, and also encapsulations in polymer substances. As with the nature of the compositions, the methods of application, such as spraying, atomising, dusting, scattering or pouring, are chosen in accordance with the intended objectives and the prevailing circumstances. The compounds I are also suitable for use in the treatment of seeds. It is possible both to treat or dress the seeds with the active ingredient or with a formulation comprising the active ingredient before sowing, and to apply the active ingredient to the furrow at the time of sowing.

The formulations, i.e. the compositions, preparations or mixtures comprising the compound (active ingredient) of formula I, or a combination of that compound with other insecticides and/or acaricides, and, where appropriate, solid or liquid adjuvants, are prepared in known manner, e.g. by homogeneously mixing and/or grinding the active ingredient with the adjuvants, such as extenders, e.g. solvents or solid carriers, or surface-active compounds (surfactants).

Suitable solvents are: aromatic hydrocarbons, preferably the $C_8$ to $C_{12}$ fractions of alkylbenzenes, such as xylene mixtures or alkylated naphthalenes, aliphatic or cycloaliphatic hydrocarbons, such as cyclohexane, paraffins or tetrahydronaphthalene, alcohols such as ethanol, propanol or butanol, glycols and their ethers and esters, such as propylene glycol, dipropylene glycol ether, ethylene glycol, ethylene glycol monomethyl or monoethyl ether, ketones, such as cyclohexanone, isophorone or diacetone alcohol, strongly polar solvents, such as N-methyl-2-pyrrolidone, dimethyl sulfoxide or N,N-dimethylformamide, water, and also vegetable oils such as rape oil, castor oil, coconut oil or soybean oil, or epoxidised vegetable oils such as epoxidised rape oil, castor oil, coconut oil or soybean oil; and, where appropriate, also silicone oils.

The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, for example pumice, broken brick, sepiolite or bentonite; and suitable non-sorbent carriers are calcite or sand. In addition, a great number of granulated materials of inorganic or organic nature can be used, especially dolomite or pulverised plant residues.

Depending on the nature of the compound I to be formulated, or of the combination of that compound with other insecticides and/or acaricides, suitable surface-active compounds are non-ionic, cationic and/or anionic surfactants having good emulsifying, dispersing and wetting properties. The term "surfactants" will also be understood as comprising mixtures of surfactants.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit. Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

Both so-called water-soluble soaps and water-soluble synthetic surface-active compounds are suitable anionic surfactants. Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tall oil; mention may also be made of fatty acid methyltaurin salts. More frequently, however, so-called synthetic surfactants are used, especially fatty sulfonates, fatty sulfates, sulfonated benzimidazole derivatives or alkylarylsulfonates. The fatty sulfonates or sulfates are usually in the form of alkali metal salts, alkaline earth metal salts or unsubstituted or substituted ammonium salts and generally contain a $C_8$–$C_{22}$alkyl radical, which also includes the alkyl moiety of acyl radicals; there may be mentioned by way of example the sodium or calcium salt of lignosulfonic acid, of dodecylsulfate or of a mixture of fatty alcohol sulfates obtained from natural fatty acids. These compounds also comprise the salts of sulfated and sulfonated fatty alcohol-/ethylene oxide adducts. The sulfonated benzimide sole derivatives preferably contain 2 sulfonic acid groups and one fatty acid radical containing approximately 8 to 22 carbon atoms. Examples of alkylarylsulfonates are the sodium, calcium or triethanolammonium salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 mol of ethylene oxide, or phospholipids.

The surfactants listed above are to be regarded merely as examples; many more surfactants customarily employed in formulation technology and suitable for use according to the invention are described in the relevant literature.

The pesticidal compositions usually comprise 0.1 to 99%, preferably 0.1 to 95%, of a compound I or a combination of that compound with other insecticides and/or acaricides, and 1 to 99.9%, preferably 5 to 99.9%, of a solid or liquid adjuvant, it being possible for 0 to 25%, preferably 0.1 to 20%, of the composition to be surfactants (in each case percentages are by weight). Whereas commercial products will preferably be formulated as concentrates, the end user will normally employ dilute formulations which have considerably lower active ingredient concentrations. Typical application concentrations are from 0.1 to 1000 ppm, preferably from 0.1 to 500 ppm. The rates of application per hectare are generally from 1 to 1000 g of active ingredient per hectare, preferably from 25 to 500 g/ha.

Preferred formulations have especially the following composition (throughout, percentages are by weight):

| Emulsifiable concentrates: | |
|---|---|
| active ingredient: | 1 to 90%, preferably 5 to 20% |
| surface-active agent: | 1 to 30%, preferably 10 to 20% |
| liquid carrier: | 5 to 94%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient: | 0.5 to 90%, preferably 1 to 80% |
| surface-active agent: | 0.5 to 20%, preferably 1 to 15% |
| solid carrier: | 5 to 95%, preferably 15 to 90% |
| Granules: | |
| active ingredient: | 0.5 to 30%, preferably 3 to 15% |
| solid carrier: | 99.5 to 70%, preferably 97 to 85% |

The compositions may also comprise further auxiliaries, such as stabilisers, for example vegetable oils or epoxidised vegetable oils (e.g. epoxidised coconut oil, rape oil or soybean oil), antifoams, for example silicone oil, preservatives, viscosity regulators, binders and/or tackifiers, as well as fertilisers or other active ingredients for obtaining special effects.

The following Examples serve to illustrate the invention, but do not limit the invention. Temperatures are given in degrees Celsius.

PREPARATION EXAMPLES

Examples P1

4-Chloro-4,4-difluoro-N-pyrid-2-yl-butyric acid amide (Table 1, compound no 1.1).

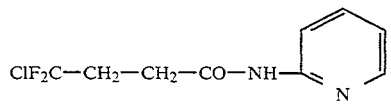

4.0 g of 4-chloro-4,4-difluoro-butyric acid chloride are added dropwise at 0° over a period of half an hour to a solution of 2.13 g of 2-aminopyridine and 4.47 g of pyridine in 50 ml of toluene. The reaction mixture is stirred for 16 hours at room temperature, diluted with 150 ml of diethyl ether, washed in succession with saturated $NaHCO_3$ solution and saturated NaCl solution, dried over $MgSO_4$, and concentrated by evaporation. The residue is recrystallised from toluene/hexane to give the title compound which melts at 64°–65°.

Example P2

In a manner analogous to that described in Example P1 it is also possible to prepare the other compounds of formula I listed in Table 1 below. In the column headed "physic. data" in that Table, the temperatures indicated denote the melting point of the compound in question.

TABLE 1

$ClF_2C-CH_2-CH_2-\underset{\underset{O}{\|}}{C}-X-A$

| Comp. No. | X | A | physic. data |
|---|---|---|---|
| 1.1 | NH | pyridin-2-yl | 64–65° |
| 1.2 | NH | 5-chloro-pyridin-2-yl | 97–99° |
| 1.3 | NH | 3-nitro-5-chloro-pyridin-2-yl | |
| 1.4 | NH | 5-bromo-pyridin-2-yl | |
| 1.5 | NH | 4,6-dimethyl-pyridin-2-yl | |
| 1.6 | NH | 3,5-dichloro-pyridin-2-yl | |

TABLE 1-continued

ClF₂C—CH₂—CH₂—C(=O)—X—A

| Comp. No. | X | A | physic. data |
|---|---|---|---|
| 1.7 | NH | 2-pyridyl | 152–153° |
| 1.8 | NH | 2-chloro-5-pyridyl | 119–121° |
| 1.9 | NH | 2,6-dichloro-3-pyridyl | |
| 1.10 | NH | 4-methylpyridyl | |
| 1.11 | NH | 3-chloro-2,5,6-trifluoro-4-pyridyl | |
| 1.12 | NH | 2-pyrimidinyl | 128–129° |
| 1.13 | NH | 4,6-dichloro-2-pyrimidinyl | |
| 1.14 | NH | 4,6-dimethyl-2-pyrimidinyl | 73–74° |
| 1.15 | NH | 4-pyrimidinyl | 120–122° |
| 1.16 | NH | 5,6-dichloro-2-pyrimidinyl | |
| 1.17 | NH | 4,5-dimethyl-6-pyrimidinyl | |
| 1.18 | NH | pyrazinyl | 174–176° |
| 1.19 | NH | 1,2,4-triazinyl | |
| 1.20 | NH | 5,6-dimethyl-1,2,4-triazinyl | |
| 1.21 | NH | 4-dimethylamino-1,3,5-triazinyl | |
| 1.22 | NH | 3,5-dimethylisoxazolyl | |
| 1.23 | NH | 5-methylisoxazolyl | 158–159° |
| 1.24 | NH | 3-methylisothiazolyl | |
| 1.25 | NH | thiazolyl | 166–167° |
| 1.26 | NH | 5-phenylthiazolyl | 181–182° |
| 1.27 | NH | 5-bromothiazolyl | 192–195° |
| 1.28 | NH | 5-methylthiazolyl | 203–204° |
| 1.29 | NH | 5-nitrothiazolyl | 143–145° |

TABLE 1-continued

ClF₂C—CH₂—CH₂—C(=O)—X—A

| Comp. No. | X | A | physic. data |
|---|---|---|---|
| 1.30 | NH | 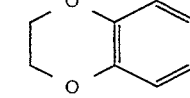 | |
| 1.31 | NH | 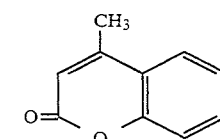 | 205–206° |
| 1.32 | NH | (thiadiazole with CF₃) | |
| 1.33 | NH | (thiadiazole with CH₃) | |
| 1.34 | NH | (quinoline) | 162–163° |
| 1.35 | NH | (quinoline) | |
| 1.36 | NH | (quinoline) | |
| 1.37 | NH | (quinoline) | |
| 1.38 | NH | (4-methylquinoline, CH₃) | |
| 1.39 | NH | (isoquinoline) | |
| 1.40 | NH | (methoxy-isoquinoline, OCH₃) | |
| 1.41 | NH | (benzodioxine) | |
| 1.42 | NH | (coumarin with CH₃) | |
| 1.43 | NH | (coumarin with CF₃) | |
| 1.44 | NH | (dimethylnaphthyridine, CH₃, CH₃) | |
| 1.45 | NH | (benzothiophene with C₂H₅O—CO) | |
| 1.46 | NH | (benzothiadiazole) | |
| 1.47 | NH | (benzothiazole) | 214–216° |
| 1.48 | NH | (benzothiazole, OCH₃) | |
| 1.49 | NH | (benzothiazole, NO₂) | 187–189° |
| 1.50 | NH | (benzothiazole, Cl) | |
| 1.51 | NH | (benzothiazole, Cl) | |

TABLE 1-continued $$ClF_2C-CH_2-CH_2-\underset{\underset{O}{\|}}{C}-X-A$$

| Comp. No. | X | A | physic. data |
|---|---|---|---|
| 1.52 | NH | (2-oxy-4-chlorophenyl)methanimine structure | 168–169° |
| 1.53 | NH | 3-methyltetrahydrofuran-2-one structure | 102–104° |
| 1.54 | NH | 3-methylazepan-2-one (caprolactam) structure | 198–199° |
| 1.55 | NH | 4-methyl-1-benzylpiperidine structure | |
| 1.56 | NH | 4-methyl-1-(ethoxycarbonyl)piperidine structure | |
| 1.57 | S | 5-(thiophen-2-yl)-1,3,4-oxadiazole structure | 114–116° |
| 1.58 | S | 5-(pyridin-3-yl)-1,3,4-oxadiazole structure | 93–95° |
| 1.59 | S | benzothiazole structure | |
| 1.60 | S | benzoxazole structure | |
| 1.61 | NH | 1H-1,2,4-triazole structure | 228–229° |

TABLE 1-continued $$ClF_2C-CH_2-CH_2-\underset{\underset{O}{\|}}{C}-X-A$$

| Comp. No. | X | A | physic. data |
|---|---|---|---|
| 1.62 | NH | 2,2-dimethyl-3-(methylthio)-thiadiazine structure | 197–198° |

FORMULATION EXAMPLES (THROUGHOUT, PERCENTAGES ARE BY WEIGHT)

| Example F1: Emulsifiable concentrates | a) | b) | c) |
|---|---|---|---|
| compound no. 1.1 | 25% | 40% | 50% |
| calcium dodecylbenzenesulfonate | 5% | 8% | 6% |
| castor oil polyethylene glycol ether (36 mol of ethylene oxide) | 5% | — | — |
| tributylphenol polyethylene glycol ether (30 mol of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| Example F2: Solutions | a) | b) | c) | d) |
|---|---|---|---|---|
| compound no. 1.12 | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160–190° C.) | — | — | 94% | — |

These solutions are suitable for application in the form of micro-drops.

| Example F3: Granules | a) | b) | c) | d) |
|---|---|---|---|---|
| compound no. 1.1 | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingredient is dissolved in dichloromethane, the solution is sprayed onto the carrier, and the solvent is subsequently evaporated off in vacuo.

| Example F4: Dusts | a) | b) |
|---|---|---|
| compound no. 1.31 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| Example F5: Wettable powders | a) | b) | c) |
|---|---|---|---|
| compound no. 1.1 | 25% | 50% | 75% |
| sodium lignosulfonate | 5% | 5% | — |
| sodium laurylsulfate | 3% | — | 5% |

| Example F5: Wettable powders | a) | b) | c) |
|---|---|---|---|
| sodium diisobutylnaphthalene-sulfonate | — | 6% | 10% |
| octylphenol polyethylene glycol ether (7-8 mol of ethylene oxide) | — | 2% | — |
| highly dispersed silicic acid | 5% | 10% | 10% |
| kaolin | 62% | 27% | — |

The active ingredient is mixed with the adjuvants and the mixture is thoroughly ground in a suitable mill, affording wettable powders which can be diluted with water to give suspensions of the desired concentration.

| Example F6: Emulsifiable concentrate | |
|---|---|
| compound no. 1.1 | 10% |
| octylphenol polyethylene glycol ether (4-5 mol of ethylene oxide) | 3% |
| calcium dodecylbenzenesulfonate | 3% |
| castor oil polyglycol ether (36 mol of ethylene oxide) | 4% |
| cyclohexanone | 30% |
| xylene mixture | 50% |

Emulsions of any required concentration can be obtained from this concentrate by dilution with water.

| Example F7: Dusts | a) | b) |
|---|---|---|
| compound no. 1.12 | 5% | 8% |
| talcum | 95% | — |
| kaolin | — | 92% |

Ready-for-use dusts are obtained by mixing the active ingredient with the carrier and grinding the mixture in a suitable mill.

| Example F8: Extruder granules | |
|---|---|
| compound no. 1.1 | 10% |
| sodium lignosulfonate | 2% |
| carboxymethylcellulose | 1% |
| kaolin | 87% |

The active ingredient is mixed and ground with the adjuvants and the mixture is moistened with water. The mixture is extruded, granulated and then dried in a stream of air.

| Example F9: Coated granules | |
|---|---|
| compound no. 1.31 | 3% |
| polyethylene glycol (mol. wt. 200) | 3% |
| kaolin | 94% |

The finely ground active ingredients is uniformly applied, in a mixer, to the kaolin moistened with polyethylene glycol. Non-dusty coated granules are obtained in this manner.

| Example F10: Suspension concentrate | |
|---|---|
| compound no. 1.1 | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

BIOLOGICAL EXAMPLES

Example B1

Action Against *Boophilus microplus*

Adult female ticks which are replete with blood are affixed to a PVC plate and covered with a cotton-wool swab. 10 ml of an aqueous test solution containing 125 ppm of the test compound are poured over the test organisms. After this treatment, the cotton-wool swab is removed and the ticks are incubated for 4 weeks until oviposition has taken place. The activity against *Boophilus microplus* is manifested either in the females as mortality or sterility or in the eggs as ovicidal action.

In this test, compounds of Table 1 exhibit good activity. In particlar, compounds 1.1, 1.8, 1.12, 1.14, 1.18, 1.25, 1.26, 1.31, 1.47, 1.54, 1.57 and 1.61 are more than 80% effective.

Example B2

Action Against *Crocidolmia binotalis* caterpillars

Young cabbage plants are sprayed with an aqueous emulsion spray mixture containing 400 ppm of the test compound. After the spray coating has dried, each of the cabbage plants is populated with 10 caterpillars of the third stage of *Crocidolmia binotalis* and introduced into a plastics container. Evaluation is made after 3 days. The percentage reduction in the population and the percentage reduction in feeding damage (% action) are determined by comparing the treated plants and the untreated plants in respect of the number of dead caterpillars and feeding damage.

In this test, compounds of Table 1 exhibit good activity. In particular, compound 1.25 is more than 80% effective.

Example B3

Action Against *Aonidiella aurandi*

Potato tubers are populated with crawlers of *Aonidiella aurantil* (red citrus scale). Approximately two weeks later the potatoes are immersed in an aqueous emulsion or suspension spray mixture containing the test compound in a concentration of 400 ppm. After drying off the treated potato tubers, they are incubated in a plastics container. Evaluation is made after 10-12 weeks by comparing the survival rate of the crawlers of the first generation of progeny of the treated scale population with that of the untreated control batches.

In this test, compounds of Table 1 exhibit good activity. In particular, compounds 1.1, 1.2, 1.12, 1.14, 1.18, 1.23 and 1.58 are more than 80% effective.

Example B4

Action against *Nilaparvata lugens*

Rice plants are treated with an aqueous emulsion spray mixture containing 400 ppm of the test compound. After the spray coating has dried, the rice plants are populated with cicada larvae in the $L_2$ and $L_3$ stages. Evaluation is made after 21 days. The percentage reduction in the population (% action) is determined by comparing the number of surviving cicadas on the treated plants with that on the untreated plants.

In this test, compounds of Table 1 exhibit good activity. In kparticular, compounds 1.1, 1.2, 1.7, 1.8, 1.12, 1.14, 1.18, 1.23, 1.25, 1.27, 1.29, 1.31, 1.34, 1.47, 1.52, 1.54, 1.57, 1.58, 1.61 and 1.62 are more than 80% effective.

Example B5

Action Against *Tetranychus urticae*

Young bean plants are populated with a mixed population of *Tetranychus urticae* and sprayed 1 day later with an aqueous emulsion spray mixture containing 400 ppm of the test compound. The plants are then incubated for 6 days at 25° C. and subsequently evaluated. The percentage reduction in the population (% action) is determined by comparing the number of dead eggs, larvae and adults on the treated plants with that on the untreated plants.

In this test, compounds of Table 1 exhibit good activity. In particular, compounds 1.1, 1.2, 1.8, 1.12, 1.18, 1.25, 1.34 and 1.53 are more than 80% effective.

Example B6

Action Against *Anthonomus grandis* Adults

Young cotton plants are sprayed with an aqueous omulsion spray mixture containing 400 ppm of the test compound. After the spray coating has dried, each cotton plant is populated with 10 Anthonomus grandis adults and introduced into a plastics container. Evaluation is made after 3 days. The percentage reduction in the population and the percentage reduction in feeding damage (% action) is determined by comparing the treated plants and the untreated plants in respect of the number of dead beetles and feeding damage.

In this test, compounds of Table 1 exhibit good activity. In particular, compounds 1.1, 1.7, 1.12, 1.23, 1.25, 1.31, 1.52, 1.54 and 1.58 are more than 80% effective.

Example B7

Action Against *Aphis craccivors*

Pea seedlings are infested with *Aphis craccivors* and then sprayed with a spray mixture containing 400 ppm of the test compound and incubated at 20° C. Evaluation is made after 3 and 6 days. The percentage reduction in the population (% action) is determined by comparing the number of dead aphids on the treated plants with that on the untreated plants.

In this test, compounds of Table 1 exhibit good activity. In particular, compounds 1.1, 1.7, 1.8, 1.12, 1.15, 1.23, 1.57, 1.58 and 1.62 are more than 80% effective.

Example B8

Systemic Action Against *Myzus persicae*

Pea seedlings are infested with *Myzus persicae* and then placed with their roots in a spray mixture containing 400 ppm of the test compound and incubated at 20° C. Evaluation is made after 3 and 6 days. The percentage reduction in the population (% action) is determined by comparing the number of dead aphids on the treated plants with that on the untreated plants.

In this test, compounds of Table 1 exhibit good activity. In particular, compounds 1.1, 1.2, 1.12, 1.15 and 1.23 are more than 80% effective.

Example B9

Systemic Action Against *Nilaparvats lugens*

Pots containing rice plants are placed in an aqueous emulsion solution containing 400 ppm of the test compound. The rice plants are then populated with larvae in the $L_2$ and $L_3$ stages. Evaluation is made after 6 days. The percentage reduction in the population (% action) is determined by comparing the number of cicadas on the treated plants with that on the untreated plants.

In this test, compounds of Table 1 exhibit good activity. In particular, compounds 1.1, 1.2, 1.7, 1.8, 1.12, 1.14, 1.15, 1.18, 1.23, 1.25, 1.26, 1.27, 1.28, 1.29, 1.31, 1.34, 1.47, 1.49, 1.52, 1.53, 1.54, 1.57, 1.58, 1.61 and 1.62 are still more than 80% effective even at 12.5 ppm.

Example B10

Ovicidal larvicidal Action on *Heliothis vireocens*

Egg deposits of *Heliothis virescens* on cotton plants are sprayed with an aqueous emulsion spray mixture containing 400 ppm of the test compound. Evaluation is made after 8 days by comparing the percentage hatching rate of the eggs and the survival rate of the caterpillars with untreated control batches (% reduction in the population).

In this test, compounds of Table 1 exhibit good activity. In particular, compounds 1.1, 1.2, 1.7, 1.8, 1.12, 1.15, 1.18, 1.23, 1.25, 1.26, 1.27, 1.31, 1.45, 1.47, 1.49, 1.52, 1.57, 1.58 and 1.62 are more than 80% effective.

Example B11

Systemic Action Against *Nephotettix cincticeps*

Pots containing rice plants are placed in an aqueous emulsion solution containing 400 ppm of the test compound. The rice plants are then populated with larvae in the $L_2$ and $L_3$ stages. Evaluation is made after 6 days. The percentage reduction in the population (% action) is determined by comparing the number of cicadas on the treated plants with that on the untreated plants.

In this test, compounds of Table 1 exhibit good activity. In particular, compounds 1.7, 1.18, 1.23, 1.25 and 1.58 are more than 80% effective.

Example B12

Action Against *Heliothis virescens* Caterpillars

Young soybean plants are sprayed with an aqueous emulsion spray mixture containing 400 ppm of the test compound. After the spray coating has dried, each of the soybean plants is populated with 10 caterpillars of the first stage of *Heliothis virescens* and introduced into a plastics container. Evaluation is made after 6 days. The percentage reduction in the population and the percentage reduction in feeding damage (% action) is determined by comparing the treated plants and the untreated plants in respect of the number of dead caterpillars and feeding damage.

In this test, compounds of Table 1 exhibit good activity. In particular, compounds 1.1, 1.7, 1.12, 1.23 and 1.58 are more than 80% effective.

Example B13

Action against *Nephotettix cincticeps*

Rice plants are treated with an aqueous emulsion spray mixture containing 400 ppm of the test compound. After the spray coating has dried, the rice plants are populated with cicada larvae in the $L_2$ and $L_3$ stages. Evaluation is made after 21 days. The percentage reduction in the population (% action) is determined by comparing the number of surviving cicadas on the treated plants with that on the untreated plants.

In this test, compounds of Table 1 exhibits good activity. In particular, compounds 1.1, 1.18, 1.23, 1.25, 1.29, 1.31, 1.34, 1.52, 1.58 and 1.62 are more than 80% effective.

What is claimed is:

1. A compound of formula

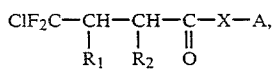 (I)

wherein

A is a substituted or unsubstituted, six member monocyclic heterocyclic radical containing two nitrogen atoms that is bonded by way of a carbon atom to X;

each of $R_1$ and $R_2$, independently of the other, is hydrogen or $C_1$–$C_8$alkyl;

X is $NR_3$, O or S; and $R_3$ is hydrogen or $C_1$–$C_4$alkyl, in free form or in salt form.

2. A compound according to claim 1 of formula I in free form.

3. A compound according to claim 2 of formula I, wherein $R_1$ hydrogen.

4. A compound according to claim 2 of formula I, wherein $R_2$ is is hydrogen.

5. A compound according to claim 2 of formula I, wherein X is $NR_3$ or S and $R_3$ is hydrogen or $C_1$–$C_4$alkyl.

6. A compound according to claim 2 of formula I, wherein the radical A that is bonded by way of a carbon atom to X is selected from the group of radicals, consisting of

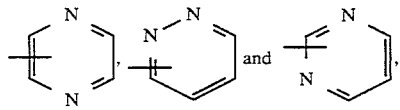

and is unsubstituted or carries one, two or three four substituents selected from the group, consisting of halogen, $C_1$–$C_6$alkyl, $C_1$–$C_4$haloalkyl having from 1 to 9 halogen atoms, $C_1$–$C_4$alkoxy, $C_1$–$C_4$haloalkoxy having from 1 to 9 halogen atoms, nitro, cyano, $C_1$–$C_4$-alkoxycarbonyl, di($C_1$–$C_4$alkyl)amino, phenyl, benzyl, pyridyl, thienyl and phenyl, benzyl, pyridyl and thienyl each mono-substituted by halogen, $C_1$–$C_4$alkyl, $C_1$–$C_4$haloalkyl having from 1 to 9 halogen atoms, $C_1$–$C_4$alkoxy, nitro or by cyano.

7. A compound according to claim 6 of formula I, wherein the radical A that is bonded by way of a carbon atom to X is selected from the group of radicals, consisting of

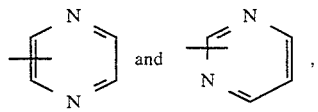

and is unsubstituted or carries one, two or three substituents selected from the group, consisting of halogen, $C_1$–$C_6$alkyl, nitro, phenyl, pyridyl and thienyl.

8. A compound according to claim 6 of formula I, wherein the radical A is selected from the group of radicals, consisting of pyrimidin-2-yl and pyrazin-2-yl, which radicals are unsubstituted or mono-substituted by halogen, methyl, pyridyl or thienyl.

9. A compound according to claim 8 of the formula

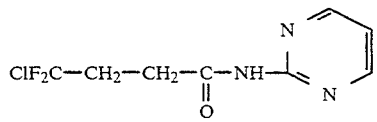

10. A compound according to claim 8 of the formula

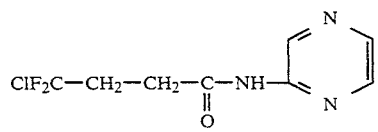

11. A pesticidal composition, comprising as pesticidally active ingredient at least one compound according to claim 1 of formula I, in free form or in agrochemically acceptable salt form, in a pesticidally effective amount, and at least one adjuvant.

12. A composition according to claim 11 for controlling insects and/or arachaids.

13. A method for controlling pests, wherein, as pesticidally active ingredient, at least one compound according to claim 1 of formula I, in free form or in agrochemically acceptable salt form, is applied, in a pesticidally effective amount, to the pests or to the locus thereof.

* * * * *